United States Patent [19]

Ram

[11] Patent Number: 5,393,229
[45] Date of Patent: Feb. 28, 1995

[54] DENTAL CLEANING IMPLEMENT INCLUDING TOOTHPICK, AND METHOD OF CLEANING TEETH THEREWITH

[76] Inventor: Zeev Ram, 9 Yaacov Street, 76 262 Rehovot, Israel

[21] Appl. No.: 75,444

[22] Filed: Jun. 14, 1993

[51] Int. Cl.⁶ .......................... A61C 1/07; A61C 3/03; A61C 3/08; A61C 15/00
[52] U.S. Cl. ..................... 433/118; 433/216; 132/322
[58] Field of Search ............. 433/80, 119, 118; 601/142, 162; 15/22.2, 22.3, 110, 167.1; 132/322

[56] References Cited

U.S. PATENT DOCUMENTS

| | | | |
|---|---|---|---|
| 3,133,351 | 5/1964 | Von Seggern | 433/119 |
| 3,335,443 | 8/1967 | Parisi et al. | 433/119 X |
| 3,636,947 | 1/1972 | Balamuth | 601/142 X |
| 3,828,770 | 8/1974 | Kuris et al. | 601/142 |
| 4,333,197 | 6/1982 | Kuris | 433/119 X |
| 4,505,676 | 3/1985 | Gonser | 433/119 |
| 4,576,190 | 3/1986 | Youssef | 132/322 |
| 4,735,200 | 4/1988 | Westerman | 15/22.2 X |
| 4,903,688 | 2/1990 | Bibby et al. | 433/216 X |
| 4,991,249 | 2/1991 | Suroff | 433/119 X |
| 5,029,358 | 7/1991 | Zimmerman | 15/167.1 |

*Primary Examiner*—Nicholas D. Lucchesi
*Attorney, Agent, or Firm*—Benjamin J. Barish

[57] ABSTRACT

A dental cleaning implement includes a handpiece graspable at one end by a user, an electrical oscillating drive within the handpiece for oscillating the handpiece at a frequency of at least 5 Khz, a head at the opposite end of the handpiece including attaching apparatus for releasably attaching a toothpick or toothbrush thereto, and a spray nozzle for discharging a liquid spray in the region of the toothpick or toothbrush when attached to the head.

17 Claims, 1 Drawing Sheet

U.S. Patent
Feb. 28, 1995
5,393,229
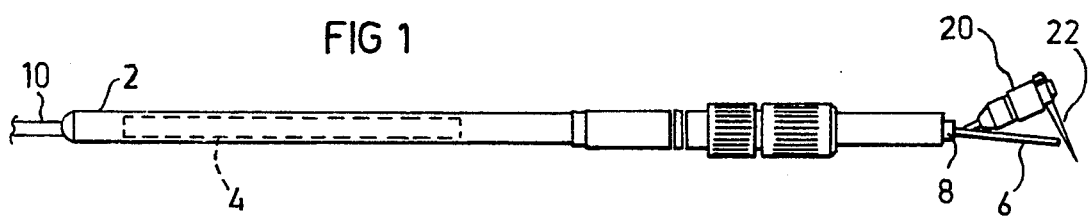
FIG 1
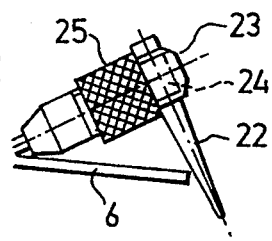
FIG. 2
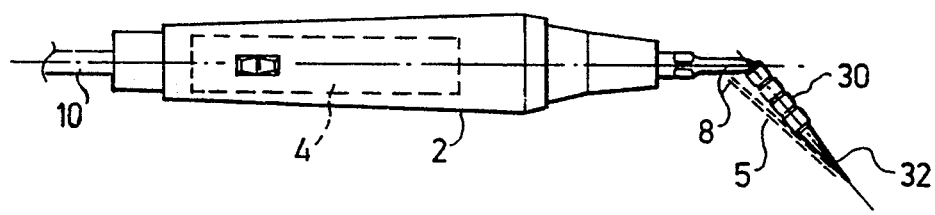
FIG. 3
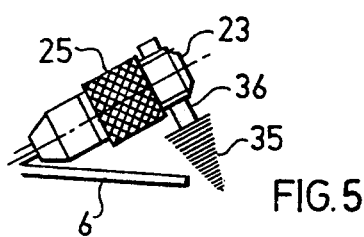
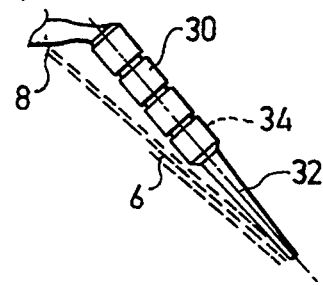
FIG. 5
FIG. 4
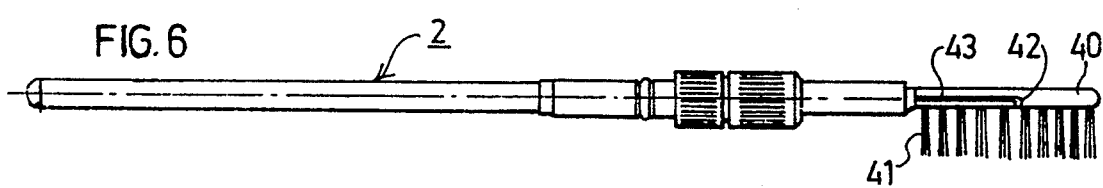
FIG. 6

DENTAL CLEANING IMPLEMENT INCLUDING TOOTHPICK, AND METHOD OF CLEANING TEETH THEREWITH

FIELD AND BACKGROUND OF THE INVENTION

The present invention relates to a dental cleaning implement including a toothpick, and to a method of cleaning teeth with such implement.

One type of dental cleaning implement now widely used in prophylaxis treatments, periodontia, and other areas of operative dentistry, includes a handpiece having an oscillating drive and a metal tip which is used with a water spray for dislodging calculus and stain. The oscillating drive is operated at ultrasonic frequencies to produce extremely rapid microscopic strokes which are transmitted to the metal tip. At the same time, the water spray is applied to flush away the dislodged calculus, soft tissue, debris, and stain, and also to cool the region. An example of such a dental cleaning implement is the Dentsply/Cavitron Model 2002 produced by the Cavitron Divison of CooperCare Inc., Palo Alto, Calif.

OBJECTS AND BRIEF SUMMARY OF THE INVENTION

According to the present invention, there is provided a dental cleaning implement comprising: a handpiece graspable at one end by a user; an electrical oscillating drive within the handpiece for oscillating the handpiece at a frequency of at least 5 Khz; a head at the opposite end of the handpiece including attaching means for releasably attaching a toothpick thereto; and a wooden toothpick releasably attached to said attaching means.

I have found that a number of important advantages over the metal tip type dental implement can be obtained by utilizing a dental implement constructed in accordance with the foregoing features. Thus, a dental cleaning implement so constructed can be used not only for cleaning the space between teeth, but also the space (called the sulcus) between the teeth and the gums. In addition, such a cleaning implement, using a wooden toothpick, enables the patient himself or herself to clean the teeth, the space between the teeth, and the space between the teeth and gums, with no pain, high cleaning efficiency, and a low danger of injury, thereby obviating the need to make visits to the dentist for this purpose. Such a dental cleaning implement may also be used for cleaning implants, porcelain crowns, bridges, etc., with reduced danger of damage, as compared for example where a metal tip implement is used. A still further advantage is that it may use a toothpick coated (or impregnated) with various types of dental reagents, as will be described more particularly below.

The releasable attaching means may also be used for attaching a toothbrush thereto when it is desired to brush the teeth.

According to further features in the described preferred embodiments, the implement further includes a spray nozzle at the opposite end of the handpiece for discharging a liquid spray (e.g., water or other therapeutic medical solution) in the region of the toothpick when attached to the head.

One embodiment is described below for purposes of example, wherein the releasable attaching means attaches the toothpick substantially perpendicularly to the axis of the head. In this described embodiment the releasable attaching means includes a stem formed with a transverse bore for receiving a toothpick, and a sleeve movable with respect to the stem to clamp the toothpick within the bore.

A second embodiment is described below wherein the releasable attaching means attaches the toothpick substantially coaxially with respect to the head. In this described embodiment, the releasable attaching means comprises a socket formed in the end of the head for receiving one end of a toothpick with a friction fit.

According to another aspect of the present invention, there is provided a dental cleaning implement in accordance with the above features in combination with a toothpick removably attached to the head.

The invention also provides toothpicks coated with various reagents particularly for use with such a dental cleaning implement, but also usable as conventional toothpicks. The description below includes examples of many reagents which may be applied as a coating (or impregnant) to the toothpicks.

According to a further aspect, the invention also provides a method of cleaning teeth using the above-identified dental implement.

Further features and advantages of the invention will be apparent from the description below.

BRIEF DESCRIPTION OF THE DRAWINGS

The invention is herein described, by way of example only, with reference to the accompanying drawings, wherein:

FIG. 1 illustrates one form of dental cleaning implement constructed in accordance with the present invention and including a toothpick;

FIG. 2 is an enlarged fragmentary view illustrating one end of the dental implement of FIG. 1;

FIG. 3 illustrates a second form of dental cleaning implement constructed in accordance with the present invention and including a toothpick;

FIG. 4 is an enlarged fragmentary view illustrating one end of the dental implement of FIG. 3;

and FIGS. 5 and 6 illustrate the dental implement as used for attaching thereto two types of toothbrushes, instead of a toothpick.

DESCRIPTION OF PREFERRED EMBODIMENTS

The dental cleaning implement illustrated in FIGS. 1 and 2 is very similar to the ultrasonic cleaning implement referred to in the introductory portion of the specification, such as the Dentsply/Cavitron Model 2002. It includes a handpiece 2 graspable at one end by a user, and an electrical oscillating drive, schematically shown by broken lines 4 in FIG. 1, within the handpiece. In the conventional dental cleaning implement referred to above, the opposite end of the handpiece includes a metal tip which is used with a water spray, schematically shown at 6, discharged from a spray nozzle 8 for cleaning the area and cooling the tip. The water is supplied to the spray nozzle 8 by a water conduit 10 which feeds the water through the handpiece 2 and thereby warms it before it is discharged from the spray nozzle 8.

Conduit 10, supplying the water (or other liquid) to the spray nozzle 8, also includes electrical conductors for supplying electrical energy to the oscillating drive 4 within the handpiece 2. The oscillating drive oscillates the handpiece at a frequency of at least 5–50 Khz, preferably of about 25 KHz. As one example, the oscillating drive 4 may be a magnetrostrictive stack which converts electrical power supplied to the handpiece via conduit 10 into mechanical oscillations at an ultrasonic frequency.

The dental cleaning implement illustrated in FIG. 1, insofar as described above, may be one of the commercially-available implements, and therefore further details of its construction and operation are not set forth herein.

In the commercially-available implements, however, the working end of the handpice 2 carries a metal tip which is used with the water spray for removing the calculus and stain, as described above. In the implement of the present invention, this metal tip is replaced by a head for removably receiving a wooden toothpick, or a toothbrush as described below with respect to FIGS. 5 and 6. In the example illustrated in FIGS. 1 and 2, a toothpick 22 is used instead of the metal tip conventionally included in this type of dental implement. Such a wooden toothpick, when used in combination with the water spray 6 discharged from the nozzle 8, has been found to effectively clean the teeth, the space between the teeth, and the space between the teeth and the gums (the sulcus).

Head 20 is more particularly seen in FIG. 2. It includes a stem 23 formed with a transverse bore 24 extending therethrough for receiving the toothpick 22. The head 20 further includes a sleeve 25 which is movable with respect to the stem 23 in one direction (rightwardly, FIG. 2) to clamp the toothpick 22 within bore 24, and in the opposite direction to release the toothpick from the bore and thereby to permit its removal and replacement with another toothpick.

In the example illustrated in FIGS. 1 and 2, sleeve 25 is retained in either its clamping position or releasing position by a friction fit with respect to stem 23. It will be appreciated, however, that other retaining means could be used, e.g., screw threads, ball-and-detent retainers, etc.

In the example illustrated in FIGS. 1 and 2, the axis of the head 20 is at an angle of about 20° to the axis of the handpiece 2, and the axis of the toothpick 22 is perpendicular to the axis of the head 20.

FIGS. 3 and 4 illustrate a variation wherein the axis of the head, therein designated 30, is also at an angle to the axis of the handpiece 2, but the toothpick, therein designated 32, is coaxial with the axis of the head 30. Thus, as shown particularly in FIG. 4, the head 30 is formed with a socket 34 which frictionally receives one end of the toothpick 32.

The cleaning implement illustrated in FIGS. 3 and 4 is otherwise of the same construction as described above with respect to FIGS. 1 and 2, and therefore corresponding parts have been correspondingly numbered to facilitate understanding.

The toothpicks, 22, 32, are made of wood. Preferably, they are coated (or impregnated) with one or more of the following reagents: a topical anesthetic, such a ethyl aminobenzoate and benzalkonium chloride; olive oil or other oil which enhances the removal of bacterial plaque from the teeth, the space between the teeth, and the space between the teeth and gums; a fluoride, to increase the resistance of the teeth to decay; a color-change pH indicator, such as phenol ftalein, to indicate an acidic or basic condition in the mouth, which can frequently aid in determining the subject's health condition; an antibiotic, such as tetracyline; an antiflammatory such as indometacine; a sensitivity-reducing reagent, such as amine fluoride; or an anticalculus reagent, such as anti-formin/citric acid or pyrophosphate.

Since the dental cleaning implements described above do not include a metal tip, but rather include a wooden toothpick, there is substantially less danger of causing injury to the teeth or to the gums; such implements may therefore also be used by the patient, thereby obviating the need for a visit to the dentist for this purpose. In addition, it was found that such implements including a wooden toothpick enable effective cleaning, and without pain, not only of the teeth and between the teeth, but also in the space between the teeth and the gums (the sulcus), something which was difficult to accomplish using the conventional implement having a metal tip. The illustrated implements were also found capable of cleaning implants, porcelain crowns, bridges, etc., with reduced danger of damage as compared to the conventional implement. Finally, by using toothpicks coated or impregnated with one of the reagents described above, the treatment of the teeth can be further enhanced and/or the toothpick can be used for diagnosing the medical condition of the patient.

FIG. 5 illustrates the dental implement as described above with respect to FIGS. 1 and 2, when used for attaching a toothbrush 35 to its head 25, rather than a toothpick in order to permit the dental implement also to be used for brushing teeth. To facilitate understanding, the same parts corresponding to those in FIGS. 1 and 2 have been identified by the same reference numerals. It will be seen from FIG. 5 that the toothbrush 35 has a stem 36 attached to the head 25 in the same manner as the toothpick 22 in FIGS. 1 and 2, and that the toothbrush 35 includes a conical array of bristles.

FIG. 6 illustrates another type of toothbrush, generally designated 40, applied to the handle 2 of the implement, e.g., by a friction fit. In this case, the toothbrush 40 includes a linear array of bristles 41 for use in brushing the teeth. The toothbrush 40 in FIG. 6 may be secured to the implement by a friction fit, similar to the arrangement described above with respect to FIGS. 3 and 4. However, in this construction the spray nozzle, therein designated 42, is located in the toothbrush 40 within its bristles 41, and is connected by a conduit 43 to the liquid supplied from the handle 2 of the implement, so that the spray nozzle discharges the liquid spray through the bristles towards the teeth when being brushed.

While the invention has been described with respect to several preferred embodiments, it will be appreciated that these are set forth merely for purposes of example, and that many other variations, modifications and applications of the invention may be made.

What is claimed is:

1. A dental cleaning implement, comprising:
   a handpiece graspable at one end by a user;
   an electrical oscillating drive within the handpiece for oscillating the handpiece at a frequency of at least 5 Khz;
   a head at the opposite end of the handpiece for releasably attaching a toothpick thereto;
   and a wooden toothpick removably attached to said head.

2. The dental cleaning implement according to claim 1, further including a spray nozzle at said opposite end of the handpiece for discharging a liquid spray in the region of the toothpick when attached to said head.

3. The dental cleaning implement according to claim 1, wherein said toothpick is releasably attached to said head substantially perpendicularly to the axis of said head.

4. The dental cleaning implement according to claim 3, wherein said head includes a stem formed with a transverse bore for receiving the toothpick, and a sleeve movable with respect to said stem to clamp the toothpick within the bore.

5. The dental cleaning implement according to claim 1, wherein said toothpick is releasably attached to said head substantially coaxially with respect to said head.

6. The dental cleaning implement according to claim 5, wherein said head comprises a socket formed in an end of said head for receiving one end of the toothpick with a friction fit.

7. The dental cleaning implement according to claim 1, wherein the axis of said head is at an angle to the axis of said handpiece.

8. The dental implement according to claim 1, wherein said toothpick is coated with a dental reagent.

9. The dental implement according to claim 8, wherein said dental reagent is a topical anesthetic.

10. The dental implement according to claim 8, wherein said dental reagent is an oil enhancing the removal of bacterial plaque.

11. The dental implement according to claim 8, wherein said dental reagent is a fluoride to increase the resistance of the teeth to decay.

12. The dental implement according to claim 8, wherein said dental reagent is a color-changeable pH indicator, which indicates an acidic or basic condition in the mouth of the user by using the toothpick.

13. The dental implement according to claim 8, wherein said dental reagent is an antibiotic.

14. The dental implement according to claim 8, wherein said dental reagent is an anti-inflammatory sensitivity-reducing reagent.

15. The dental implement according to claim 8, wherein said dental reagent is an anti-calculus reagent.

16. A method cleaning teeth, comprising:
grasping a dental implement including a handpiece, and an electrical oscillating drive within the handpiece for oscillating the handpiece at a frequency of at least 5 Khz, a head at an end of the handpiece for releasably attaching a wooden toothpick thereto, and a toothpick releasably attached to said head;
and applying said wooden toothpick to the space between the teeth, and also to the space between the teeth and gums, while oscillating the toothpick at a frequency of at least 5 Khz.

17. The method of claim 16, including the further step of discharging a spray of a liquid in the region of the toothpick while being used to clean the teeth.

* * * * *